(12) United States Patent
Randhava et al.

(10) Patent No.: US 8,791,165 B2
(45) Date of Patent: Jul. 29, 2014

(54) SYNTHESIS OF DME USING A FLUID PLURALIZED BED REACTOR

(75) Inventors: Sarabjit S. Randhava, Evanston, IL (US); Richard L. Kao, Northbrook, IL (US); Todd L. Harvey, Schaumburg, IL (US)

(73) Assignee: Unitel Technologies, Inc., Mt. Prospect, IL (US)

( * ) Notice: Subject to any disclaimer, the term of this patent is extended or adjusted under 35 U.S.C. 154(b) by 446 days.

(21) Appl. No.: 13/197,342

(22) Filed: Aug. 3, 2011

(65) Prior Publication Data

US 2013/0035406 A1    Feb. 7, 2013

(51) Int. Cl.
     *C07C 27/06*      (2006.01)
     *C07C 41/09*      (2006.01)

(52) U.S. Cl.
     CPC ..................................... *C07C 41/09* (2013.01)
     USPC ........... 518/700; 518/702; 518/703; 518/704

(58) Field of Classification Search
None
See application file for complete search history.

(56) References Cited

U.S. PATENT DOCUMENTS

2013/0035406 A1    2/2013   Randhava

*Primary Examiner* — Sudhakar Katakam (57) ABSTRACT

This invention discloses a method for making a dimethylether (DME) product from a synthesis gas (syngas) in the presence of a catalyst in a fluid pluralized bed reactor operating in the gas phase. The reactions generate a significant amount of heat and the heat management is balanced between supplying quench recycle syngas to the pluralized sections along the reactor and also by controlling the preheat temperature of the reactant streams. Gas phase fluidization of the catalyst is controlled so that the pluralized reactive zones are maintained in a backmix configuration.

15 Claims, 4 Drawing Sheets

SYNTHESIS OF DME USING A FLUID PLURALIZED BED REACTOR

REFERENCES CITED

| U.S. Pat. No. 4,417,000 | November 1983 | Slaugh et al. |
| U.S. Pat. No. 5,254,596 | October 1993 | Irick, Jr. et al. |
| U.S. Pat. No. 5,908,963 | June 1999 | Voss et al. |
| U.S. Pat. No. 6,191,175 | February 2001 | Haugaard et al. |

Lu, W. Z., Teng, L. H., Xiao, W. D., 2002. Simulation analysis of fixed-bed reactor for dimethyl ether synthesis. Natural Gas Chemical Industry 27 (4), 53-61

U.S. Pat. No. 5,218,003 June 1993 Lewnard et al.

US Patent Application Publication No. 2005/0038129 A1 February 2007 Lattner

Brown, D. M., Bhatt, B. I., Hsiung, T. H., 1991. Novel technology for the synthesis of dimethyl ether from syngas. Catalysis Today 8, 279-304

Guo, Q. G., Huang, Y. M., 1997. Studies on preparation of the catalyst for synthesizing of low carbon olefin from $CO+H_2$. Natural Gas Chemical Industry (C1 Chemistry and Technology), 22(2)25-29

Wang, Z. L., Wang, J. F., Diao, J., Jin, Y., 2001. The synergy effect of process coupling for dimethyl ether synthesis in slurry reactors. Chemical Engineering & Technologies 24 (5), 507-511.

Liu, D. H., Xu, J. Zhang, H. T. Fang, D. Y. 2002 Direct synthesis of dimethyl ether from syngas in three phase agitated reactors. Chinese Journal of Chemical Engineering. 53(1): 103-106.

Takashi Ogawa, Norio Inoue, Tutomu Shikada, Yotario Ohno, 2003. Direct Dimethyl Ether Synthesis. Journal of Natural Gas Chemistry 12, 219-227.

Xiao, W. D., Lu, W. Z., 2002. A Novel Technology of DME Synthesis from Syngas. Patent No. CN1332141, China.

Lu, W. Z., Teng, L. H., Xiao, W. D., 2004. Simulation and experiment study of dimethyl ether synthesis from syngas in a fluidized-bed reactor. Chemical Engineering Science 59, 5455-5464.

FIELD OF THE INVENTION

This invention relates to the production of dimethylether (DME). In particular, this invention relates to the production of DME using a fluid pluralized bed reactor.

BACKGROUND OF THE INVENTION

Current technology proposed three kinds of reactor for DME synthesis: the fixed bed (U.S. Pat. Nos. 5,254,596; 4,417,000; 5,908,963; 6,191,175; Xiao et al., 2002; Lu et al., 2002), the slurry reactor (U.S. Pat. No. 5,218,003; US Patent Application Publication No. 2005/0038129 A 1; Brown et al., 1991; Guo, et al., 1997; Wang, et al., 2001; Liu, et al., 2002; Takashi, et al., 2003) and the fluid bed reactor (Xiao, et al., 2002; Lu, et al., 2004). The process for making DME from a hydrogen and carbon monoxide syngas mixture is highly exothermic. The fixed bed reactor can only provide a limited heat removal capability, thus only a low conversion of the syngas can be achieved. At the conditions of P=4 MPa (565 psig), $H_2/CO$ molar ratio of 1.0, and gas space velocity of 15,000 ml/gcat/hr to keep the reactor temperature below 270° C. (518° F.), a fixed bed only yields 10.7% CO conversion and 91.9% DME selectivity (Lu, et al., 2002). On the contrary, the slurry reactor can provide an effective temperature control, but the two mass transfer resistances through the gas-liquid and the liquid-solid interfaces limit the DME productivity. In a slurry reactor under the conditions of T=260° C. (500° F.), P=4 MPa (565 psig), $H_2/CO$ molar ratio of 1.0, and gas space velocity of 3,000 ml/gcat/hr, the CO conversion and DME selectivity are 17.0% and 70.0% (Wang, et al., 2001).

In a fluid bed reactor, the gas-solid mass transfer resistance is so small that it can be neglected. Excellent temperature control is also achievable due to the vigorous mixing of catalyst particles in the fluid bed. Compared to a fixed bed or a slurry bed under the same conditions of the slurry bed, the CO conversion and DME selectivity in a fluid bed are 48.5% and 97.0% (Lu, et al., 2004). Therefore, the fluid bed reactor is the most promising for production of DME from syngas.

In this invention an improved embodiment to the fluid bed reactor called "fluid pluralized bed reactor" is described in the following sections, figures and examples to further promote effective removal of reaction heat in the reactor in order to minimize the recycle flow rate within the DME synthesis loop.

SUMMARY OF THE INVENTION

This invention provides a fluid pluralized bed reactor for producing DME from syngas. In particular, a relatively even temperature profile is achieved by the balancing of the heat generated within the reactor during the syngas to DME synthesis against the heat needed to bring the make-up syngas and recycle gas up to the desired DME reaction temperature.

The fluid pluralized bed is well mixed to provide proper heat transfer. In one embodiment, proper mixing is attained within the reactor by a combination of superficial velocities, aspect ratio of the catalyst bed and the catalyst particle size and density.

The fluid pluralized bed reactor temperature can be controlled either with or without the internal heat transmission tube in the reactor. A higher recycle rate is required when there is no internal heat transmission tube in the reactor.

The kinetics of the reaction are such that the bulk of the reaction is typically completed within a short distance downstream of the entry of the feed gases. In order to spread the reaction kinetics in a more isothermal fashion, it is convenient and appropriate to be able to introduce the feed gases in controlled quantities at several sections along the reactor. The feed gases in that case serve to also quench the reactor temperatures and bring them somewhat closer to an isothermal mode.

Each gas quench section also generates an environment of backmixing of catalyst solids that effectively distributes the heat generated uniformly throughout the bed. The circulating pattern of the catalyst lifts the catalyst upwards initially, picking up heat of reaction. This catalyst then circulates downwards to meet the fresh feed gases and preheat them quickly to reaction temperatures. The deployment of catalyst solids in this fashion greatly simplifies the kinetics and reduces or eliminates the amount of overall heat transfer surface area needed to control the process.

Appropriate injection of quench recycle syngas into different sections along the reactor then creates a series of independent, yet connected, backmix environments for optimizing the reactions and isothermality. In each section, temperature management can further be conducted by controlling the incoming temperature of the make-up syngas—whether they need to be cooled or heated is a function of the catalyst. In one embodiment of the invention, the fluid pluralized bed reactor is maintained at a temperature ranging from 150° C. to 350° C. (302° F. to 662° F.). Preferably, it is maintained at a temperature of 180° C. to 320° C. (356° F. to 608° F.), more preferably from 200° C. to 280° C. (392° F. to 536° F.).

In one embodiment, the temperature of the fluid pluralized bed is maintained by controlling the temperature of the feed gases entering the reactor through the reactor bottom gas distributor. In another embodiment, the feed gases may be entering the reactor at several different sections. The temperatures of the different incoming feed gas streams may be independently controlled to generate axial isothermality of the reactor. Preferably, the make-up syngas stream flowing into the reactor enters at ambient temperature, 37.8° C. (100.0° F.) while the recycle syngas enters at methanol absorber outlet temperatures ranging from −21° C. to −5° C. (−6° F. to 23° F.).

DETAILED DESCRIPTION OF THE INVENTION

Exothermicity & Equilibrium Considerations

The process of making dimethylether (DME) from a hydrogen and carbon monoxide syngas mixture is a strongly exothermic and equilibrium dictative reaction. Under LeChatelier principles, this process requires relatively high operating pressures and low temperatures to attain reasonable rates of reaction.

|  | | $\Delta H$ | Exothermic Heat |
|---|---|---|---|
| Methanol Synthesis from CO $2CO + 4H_2 \Leftrightarrow 2CH_3OH$ | (1) | −197.48 kJ/mole* | 74% |
| Methanol Dehydration to DME $2CH_3OH \Leftrightarrow CH_3OCH_3 + H_2O$ | (2) | −21.26 kJ/mole | 10% |
| Water Gas Shift $CO + H_2O \Leftrightarrow CO_2 + H_2$ | (3) | −39.57 kJ/mole | 16% |
| Overall DME Synthesis Reaction Direct DME from Syngas Producing $CO_2$ $3CO + 3H_2 \Leftrightarrow CH_3OCH_3 + CO_2$ |  | −258.31 kJ/mole | 100% |

*1 KJ/mole = 430.21 Btu/lb mole

All the three reactions are reversible and release a significant amount of heat for all these forward reactions. Consequently, a critical factor for DME reactor design is the management of the heat released by the reactions. The heat released by DME production can generate 2.4 tons of steam per ton of DME, equivalent to an adiabatic temperature rise of about 1,000° C. (1,832° F.) at a complete conversion of syngas with a 1:1 molar ratio of $H_2$:CO in the feed gas.

However, the catalyst for Reactions (1) and (3) is subject to severe deactivation when overheated to above 280° C. (536° F.). To avoid thermodynamic limitations and excessive catalyst deactivation, conventional gas-phase reactors must be operated at a low per-pass conversion to maintain reactor temperature below 280° C. (536° F.), implementing a high syngas recycle rate, and resulting in large capital investments and operating costs.

Under such reaction conditions, the attainable conversion is strongly limited by the thermodynamic equilibrium. Finding a satisfactory compromise as to the reaction conditions between reaction rate and conversion percentage is therefore difficult. Effective control of the reaction temperature across the catalyst bed proved to be a technically problematic consideration.

In industrially applied processes, in which the catalyst is present in the form of a fixed bed of particles, high gas velocities are applied to promote effective removal of reaction heat and to allow good control of the reaction temperature. Due to these high velocities and the thermodynamic limitations, low CO conversions per pass are obtained. To achieve acceptable yields of DME from synthesis gas it is customary to recompress unconverted synthesis gas and recycle it to the reactor inlet. This requires recycle compressors of large capacities, which are costly and have high power consumptions. It is because of these constraints that using a fluid pluralized bed becomes an optimal solution.

Fluidization

The description of fluidization, its characteristics and attributes are based upon the seminal work of D. Kunii and O. Levenspiel, Fluidization Engineering, 1977.

Figure 1:
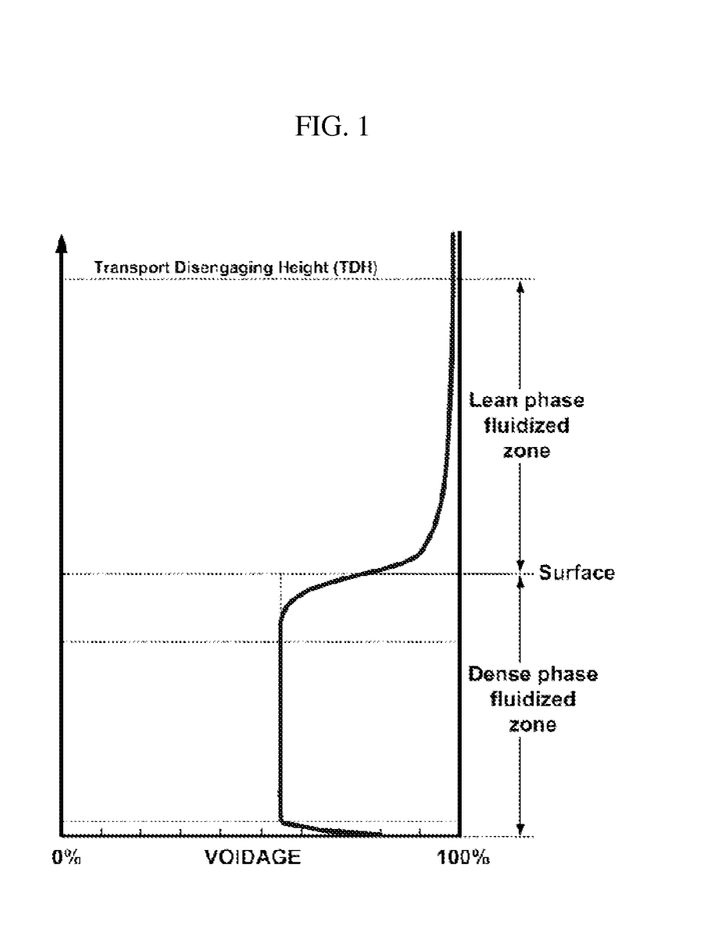
FIG. 1 is the voidage variation along the height of a fluid pluralized bed.

Voidage variation along the height of a bubbling-fluid pluralized bed is carefully understood and implemented in the design and layout of the gas distributors. Broadly speaking, the bed comprises of two zones—a dense bubbling zone, and a lean fluidizing zone (FIG. 1). The bubbling zone has a lower entrance zone that has a slightly decreased solids density due to the adjacent gas distributor, and a main zone of constant density. An increase in gas velocity results in a linear decrease in bed density, and a commensurate increase of the height of constant density zone.

A dense bubbling bed has regions of low solid density, sometimes called gas pockets or voids. These regions are called bubble phase. The region of higher solid density is called the emulsion region or the dense phase. Within the dense phase, there is also an on-going solids circulation phenomena that is conventionally referred to as backmixing. Additionally, based upon the fluidization gas velocities, the bed may be operating in a bubbling, slugging or turbulent fluidization regime. Maximization of the backmixing phenomena is preferably attained under turbulent fluidization conditions.

At a certain height, the bubbling bed transitions into a lean fluidized zone of decreasing densities. There is minimal entrainment at the top of the lean fluidized zone and at a certain height the particulate entrainment becomes approximately constant. This is referred to as the transport disengaging height (TDH) and this is where the vessel exit is positioned. When an internal cyclone is used, the unit is placed below the TDH position and this results in an economy regarding the overall height and cost.

In practice, the gaseous reactant products leaving the top of the fluid pluralized bed are directed into a disengaging zone to separate the catalyst fines from the gases. In one embodiment, one or more cyclones are located below the TDH in the upper portion of the reactor. The cyclones are equipped with diplegs with the leg of the primary cyclone dropping into the bottom section of the fluid pluralized bed and the leg of the secondary or fine cyclone dropping into an area of the fluid pluralized bed above the prior dipleg.

Other embodiments for particulate separation may also be satisfactorily utilized. These embodiments include the use of blow back filters, either internal to the reactor or external. Other embodiments include increasing the height of the reactor and various other methods including meshes, plates, etc. In all cases, the fines separated by an appropriate embodiment should be directed back into the fluidized catalyst section.

Fluidization Parameters

Particle size is an important property that contributes to appropriate fluidization and appropriate backmixing of the catalyst within the designated reactor bed/section. In one embodiment of the invention, the catalyst bed includes catalyst particles having a particle size (i.e., average diameter) of from 20 to 300 microns. Preferably, the catalyst particles have a particle size of from 50 to 200 microns.

Superficial gas velocity (SGV) is a measurement of the gas flowing through the catalyst bed. It is defined as:

$$\text{Superficial gas velocity (m/sec)} = \frac{\text{Volumetric flow rate of gases leaving the reactor (m}^3/\text{sec)}}{\text{Average cross section area of the reactor (m}^2\text{)}}$$

Typically, the fluid pluralized bed reactor SGV ranges from 0.1 m/sec to 2.0 m/sec. Low SGV may result in lack of fluidization while a high SGV may convert a dense phase fluid pluralized bed into a lean phase fluid pluralized bed where the voidage becomes so excessive that it inhibits contact between the catalyst and the reactive gases resulting in significant reaction yield loss.

In one embodiment, the SGV is not greater than 1.5 m/sec and in another not greater than 1.25 m/sec. Preferably, the reactor is maintained at a SGV of 0.3 m/sec to 1 m/sec and more preferably from 0.3 m/sec to 0.5 m/sec.

Particle density is also a significant contributor in the maintenance of fluid pluralized beds. It is calculated by using the following equation.

$$\rho_p = \frac{1}{1/\rho_s + V_p} [\text{g/cm}^3]$$

$\rho_s$: the true density of the substance constituting the particles (g/cm$^3$)
$V_P$: the pore volume (cm$^3$/g)
$\rho_p$: the particle density (g/cm$^3$)

A good range for particle density in this reactor is 1.5 g/cm$^3$ to 3 g/cm$^3$.

If the particle density is more than 3 g/cm$^3$, the bed will require extremely high gas flow rates to attain a fluidized condition. Such high gas flow rates will result in low per pass conversions because the volumetric hourly space velocity will become excessive.

If the particle density is less than 1.5 g/cm$^3$, there will be a significant excess of catalyst going off into the lean phase and a small amount in the dense reactive phase. A lot of the catalyst will flow into the upper section and put a heavy burden on the cyclones and diplegs. It is possible that the catalyst layer will swell up at relatively low superficial linear velocities and flood the reactor.

Bed density is another criteria that has to be carefully considered. The bed density of the reactor is defined as the volume fraction of catalyst solids in the reactor. Generally, the catalyst in the dense phase is maintained at a solids volume fraction ranging from 0.25 to 0.6. This fraction translates to 25% to 60% of the volume in the bed is occupied by the solid catalyst particles. In the lean phase, which is above the dense phase zone, the solids void fraction typically ranges from 0.15 to 0.3, which translates into 15 to 30% volume in the bed occupied by the solid catalyst particles. Preferably, the catalyst in the dense phase is maintained at a solids volume fraction ranging from 0.4 to 0.5 and in the lean phase, the catalyst is maintained at a solids volume fraction ranging from 0.2 to 0.25.

Backmixing

Backmixing is a state in a reactor where the contents are well stirred and uniform in composition throughout. Consequently, the exit stream leaving this reactor should have the same composition as the fluid within the reactor.

Backmixing of the catalyst in this application is typically attained by utilizing proper reactor design and a combination of superficial gas velocities, aspect ratio of the catalyst bed and the catalyst particle size and density. The flow gas through the dense phase zone is adequate to keep the catalyst in the dense phase zone with sufficient backmixing. Good backmixing results in a remarkably temperature stable system without hot spots, making for a good control of the reaction. Further, the large gas solid contact area as well as good contacting of the solid-gas phases makes this an efficient system for effecting the catalytic reactions and heat transfer which achieve a low ΔT across the reactor, both radially and axially.

In addition to the proper superficial gas velocity, bed density and particle size and density as mentioned above, in order to achieve the proper level of backmixing in the dense phase bed, the aspect ratio of the catalyst bed should be kept relatively low. According to this invention, the aspect ratio is the ratio of the height of the catalyst bed to the diameter of the catalyst bed. Preferably, the dense phase bed is maintained at a catalyst bed height to diameter ratio of not greater than 10:1, more preferably not greater than 5:1, and most preferably not greater than about 2:1.

DME Fluid Pluralized Bed Reactor

The fluid pluralized bed reactor is configured to ensure that the heat generated within the reactor during the syngas to DME conversion reaction is balanced by the heat needed to bring the feed gases up to the desired temperature either with or without the internal heat transmission tube in the reactor.

The kinetics of the reaction are such that the bulk of the reaction is typically completed within a short distance downstream of the entry of the feed gases. In order to spread the reaction kinetics in a more isothermal fashion, it is convenient and appropriate to be able to introduce the feed gases in controlled quantities at several sections along the reactor. The feed gases in that case serve to also quench the reactor temperatures and bring them somewhat closer to an isothermal mode.

Each gas quench section also generates an environment of backmixing of catalyst solids that effectively distributes the heat generated uniformly throughout the bed. The circulating pattern of the catalyst lifts the catalyst upwards initially, picking up heat of reaction. This catalyst then circulates downwards to meet the fresh feed gases and preheat them quickly to reaction temperatures. The deployment of catalyst solids in this fashion greatly simplifies the kinetics and reduces the amount of overall heat transfer surface area needed to control the process.

Appropriate injection of quenched recycle syngas into different sections along the reactor then creates a series of independent, yet connected, backmix environments for optimizing the reactions and isothermality. In each section, temperature management can further be conducted by controlling the incoming temperature of the make-up syngas—whether they need to be cooled or warmed is a function of the catalyst. In one embodiment of the invention, the fluid pluralized bed reactor is maintained at a temperature ranging from 150° C. to 350° C. (302° F. to 662° F.). Preferably, it is maintained at a temperature of 180° C. to 320° C. (356° F. to 608° F.), more preferably from 200° C. to 280° C. (392° F. to 536° F.).

In one embodiment, the temperature of the fluid pluralized bed is maintained by controlling the temperature of the feed gases entering the reactor through the reactor bottom gas distributor. In another embodiment, the feed gases may be entering the reactor at several different sections. The temperatures of the different incoming feed gas streams may be independently controlled to generate axial isothermality of the reactor. Preferably, the make-up syngas stream flowing into the reactor enters at ambient temperature, 37.8° C. (100.0° F.) while the recycle syngas enters at methanol absorber outlet temperatures ranging from −21° C. to −5° C. (−6° F. to 23° F.).

The treated gas from the methanol absorber contains unconverted syngas. In order to maximize the production of DME, this gas needs to be recycled around the DME synthesis loop. A small amount of the recycle gas is purged in order to remove the accumulating inert gases in the loop.

Distributors

Kinetics in the reactor is conducted by injecting the reactant gases through appropriate distributors. The function of the distributors is to evenly distribute the reactant gases so as to fluidize the catalyst in the reactor in such a way as to maintain sufficient backmix capabilities.

There may be several distributors axially positioned approaching a logarithmic distribution along the fluid pluralized bed reactor. A reactor, for example, may typically be equipped with three distributors, one at the bottom, one at position x and one at position 10x, where x is an arbitrary axial dimension. Each distributor then generates its own fluidization characteristic along with its own backmix envelope.

Each one of the backmix envelopes that has been developed will have its independent kinetics, the commensurate heat release (these reactions are highly exothermic) and volume contraction (the overall DME synthesis reaction converts three moles of CO plus three moles of $H_2$ into one mole of DME and one mole of $CO_2$). The temperature increase within the backmix envelope along with a volumetric decrease of gas creates issues with regards to fluidization and backmix.

It has been discovered that introducing the gas through the distributors and into the reactor must be done under a temperature control algorithm where temperature sensors located in the bed directly above the distributors control the amount and the temperature of the reactant gas. The backmix characteristics of the fluid pluralized bed are normally analyzed by embedding several temperature sensors within the bed and looking at the temperature differences between the sensors. Ideally a good backmix system will exhibit the temperature differences to be approaching zero.

Figure 2:
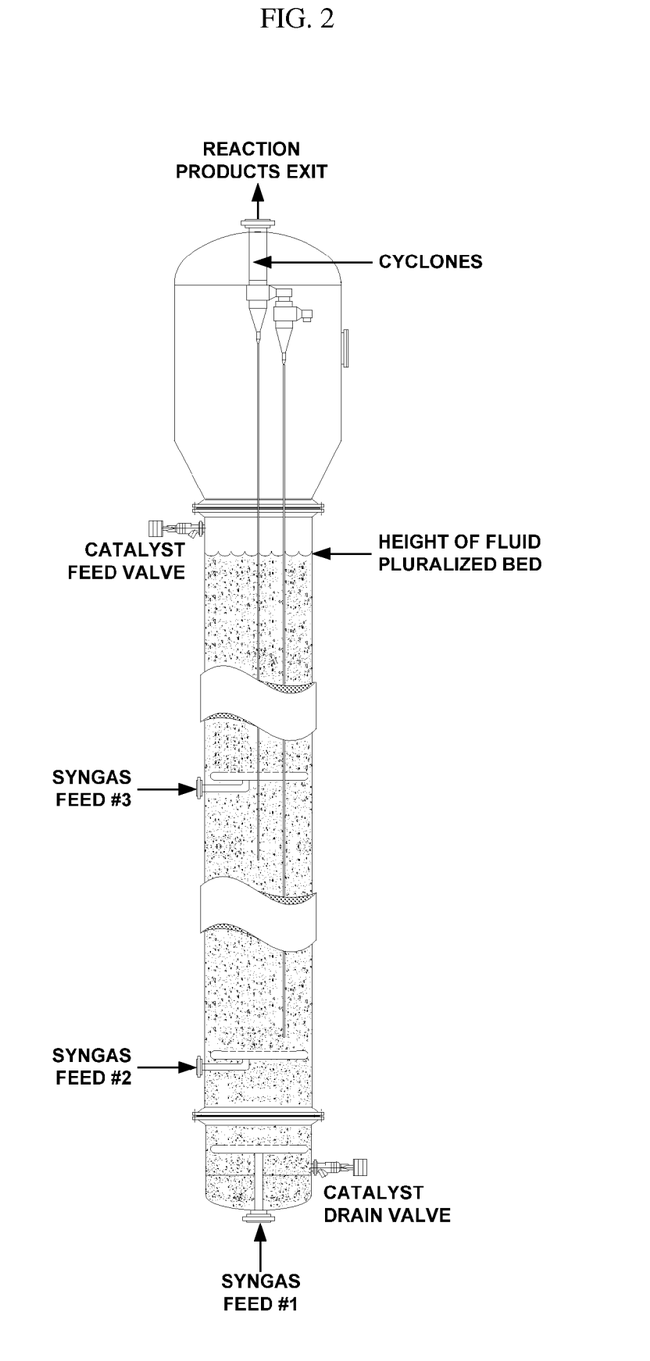
FIG. 2 is a proposed fluid pluralized bed reactor equipped with three distributors.

The proposed reactor is equipped with three distributors as shown in FIG. 2. In one embodiment of the reactor, the reactant gases enter at three sections: one at the bottom of the reactor through a distributor and two entries are along the side of the reactor at different heights. These three gas entries through their distributors results in three independent yet linked backmix reactors where the temperature is controlled not only by the temperatures of the feed gases but also by limiting the conversion of the reactants. It is obvious that at gas flow rates will also be a determinating factor of the reaction completion. Because of the highly exothermic nature of the overall reaction, it is sometimes important to control the overall mole conversion of the CO in a range from 25 to 60%. Preferably, conversions are maintained in the range from 30-55% and more preferably from 40-50%.

The fluid pluralized bed reactor is proposed as the ideal device for DME synthesis. Compared with the slurry reactor, the gas-solid mass transfer resistance in a fluid pluralized bed reactor is so small that it can be neglected, and excellent temperature control is also achievable due to the vigorous mixing of catalyst particles in the bed. Almost all of the reactions occur in the dense phase, which contains the catalyst particles, whereas the bubble phase does not contribute significantly to the reaction due to low solid concentration. Concentration gradients are established between the two phases, due to the depletion of reactants and the synthesis of products, inducing the diffusion of products from the dense phase to the bubble phase, and that of the reactants in the opposite direction.

The syngas-to-DME process is highly exothermic. A critical factor for DME reactor design is the management of the heat released by the reactions. The heat released by DME production can generate 2.4 tons of steam per ton of DME, equivalent to an adiabatic temperature rise of about 1,000° C. (1,832° F.) at a complete conversion of syngas with a 1:1 molar ratio of $H_2$:CO in the feed gas. This problem is especially significant as the catalyst of DME synthesis may be deactivated rapidly when the temperature is over 280° C. (536° F.).

Our preliminary theoretical investigation has shown that fluid pluralized bed technology is more efficient for DME synthesis than slurry reactor and fixed bed technologies. When $H_2$/CO molar ratio equals 1.0 in the feed gas, the CO conversion and DME selectivity are 48.5% and 97% in a fluid pluralized bed reactor, compared to the values of 17% and 70% in a slurry reactor under the same conditions, and to 10.7% and 91.9% in a fixed bed reactor under its normal conditions. The superior efficiency of the fluid pluralized bed results from the elimination of diffusional limitations, giving rise to an effectiveness factor very close to one, and also because of the shift of equilibrium to more favorable conditions, such as the product diffusion from the dense phase to the bubble phase.

The sensitivity simulation shows that, the effect of the mass transfer coefficient can be ignored, the optimum $H_2$/CO molar ratio in the make-up syngas is 0.9 to 1.1 while in the feed gas (make-up syngas plus recycle syngas) to the DME reactor is between 0.9 to 1.5. The enhancement of pressure improves DME productivity substantially. High temperature is also favorable for DME synthesis up to a maximum temperature of 285° C. (545° F.), past which it starts dropping gradually.

The direct conversion of the equimolar hydrogen and CO gas mixture in the make-up syngas into DME is an extremely exothermic reaction. In view of this, our reactor has been specially designed to maintain a highly isothermal profile. The DME catalyst is susceptible to rapid coking in case the operating conditions are upset for some unforeseen reason(s), therefore it's essential that the catalyst can be added or replaced with a minimum of difficulty and effort.

Catalyst

This invention uses an attrition resistant bifunctional catalyst where methanol synthesis—water gas shift reaction is one function and the methanol dehydration to DME reaction is the other function.

The procedure to manufacture of this catalyst comprises the following steps:

(a) co-precipitation preparation of $CuCO_3$, $ZnCO_3$, $CrO_2$ and $La_2(CO_3)_3$ using reagents of $Cu(NO_3)_2$, $Zn(NO_3)_2$, $Cr(NO_3)_3$, $La(NO_3)_3$ and $Na_2CO_3$ at 80° C. to a final pH value of 7, then $Al(OH)_3$ power was added to the co-precipitate, (b) preparation of a slurry with the dehydrogenation component HZSM-5, (c) addition of silica sol as binder with a particle size less than 15 nm and a pH value of 4-5 into the slurry, (d) spray drying the slurry to form microspheres and (e) calcination.

The catalyst comprises of particles having a size ranging from 20 to 300 μm and is optimized for fluid pluralized bed reactor operation.

The following examples provide data for the balancing of the heat generates within the fluid pluralized bed reactor during the syngas to DME synthesis against the heat needed to bring the make-up syngas and recycle gas up to the desired DME reaction temperature, i.e. 260° C. to 280° C. (500° F. to 536° F.) either with or without the internal heat transmission tube in the reactor. Two different absorption solvents for the removal of the acid gases generated in the DME synthesis loop were evaluated. Other options include the use of a water gas shift reactor after the autothermal reformer and the recycle of the whole DME synthesis loop purge gas to the autothermal reformer were also investigated. Finally, the pressure of the two light end columns is changed to three different pressure levels: 224.6 psig (16 bar), 347.9 psig (25 bar) and 463.9 psig (33 bar) in order to increase the condenser temperature. All the examples are given by way of illustration only and not by way of limitation to the present invention.

EXAMPLE 1

36,358 lb/hr of biomass with the composition shown below is fed to a gasifier operated at 1750° F. and 150 psig.

| Biomass Proximate Analyses | |
| --- | --- |
| Comp. | Wt % |
| Moisture | 10.000 |
| Fixed Carbon | 11.954 |
| Volatiles | 83.400 |
| Ash | 4.646 |
| Total | 110.000 |

| Biomass Ultimate Analyses | |
| --- | --- |
| Comp. | Wt % |
| Carbon | 49.454 |
| Hydrogen | 5.755 |
| Nitrogen | 0.061 |
| Sulfur | 0.024 |
| Oxygen | 40.060 |
| Ash | 4.646 |
| Total | 100.000 |

An oxidative autothermal reformer operated at 1557° F. and 144 psig is provided for the simultaneous removal of tars, benzene/toluene/xylene components, and for decreasing methane concentration by reforming while optimizing energy efficiency. A syngas with the composition below is obtained:

| Syngas from Autothermal Reformer | |
| --- | --- |
| Phase | Vapor |
| Temp., ° F. | 1556.8 |
| Pressure, psig | 144.0 |
| Flowrate, lbmol/hr | 2637.62 |
| $H_2$/CO, Molar Ratio | 0.9560 |
| Composition | Mol % |
| $CH_4$ | 2.00 |
| $CO_2$ | 14.80 |
| $N_2$ | 0.35 |
| $H_2O$ | 15.29 |
| CO | 34.54 |
| $H_2$ | 33.02 |

This gas is then cooled down to 108° F. to knock out most of its moisture content before it is compressed by a two-stage compressor with intercooler, aftercooler and water knockout to 710 psig.

The compressed syngas is then passed through an absorber using $CH_3$—O—$(CH_2CH_2O)_5$—$CH_3$ ($C_{12}H_{26}O_6$) as the absorption solvent to remove 88 mol % of the $CO_2$ in the stream. The rich solvent is regenerated by a simple flash, and no thermal energy is required. The lean gas from the absorber is combined with $H_2$ recovered from the DME synthesis loop purge gas before it is fed to a DME fluid pluralized bed reactor. Part of the heat released by the exothermic reactions (Q=−10.48×10$^6$ Btu/hr) is removed by passing a heat transfer medium through a heat transmission tube in the fluid pluralized bed. This make-up syngas having the following composition is introduced through the distributor located at the bottom of the fluid pluralized bed reactor.

| Make-up Syngas to DME Reactor | |
| --- | --- |
| Phase | Vapor |
| Temp., ° F. | 100.0 |
| Pressure, psig | 710.5 |
| Flowrate, lbmol/hr | 1766.36 |
| $H_2$/CO, Molar Ratio | 1.0095 |
| Composition | Mol % |
| $CH_4$ | 2.25 |
| $CO_2$ | 2.67 |
| $N_2$ | 0.48 |
| $H_2O$ | 0.02 |
| CO | 47.07 |
| $H_2$ | 47.51 |

Due to the efficient backmixing is maintained in the fluid pluralized bed, the fresh make-up syngas is preheated quickly to reaction temperatures. The cooled recycle gas after the purge is served as the two other entries along the side of the reactor at different heights in order to have additional control of the reaction temperatures.

The effluent from the reactor is cooled to 14° F. to condense out most of the water and methanol and about 40% of the DME product. The remaining of the DME product and most of the acid gas ($CO_2$) in the vapor phase is removed by an absorber using methanol as the absorption solvent. The stream descriptions of the condensate from the condenser and rich solvent from methanol absorber are shown below.

| Crude DME Product | | |
|---|---|---|
| Stream | Condensate from the Condenser | Rich Solvent from Methanol Absorber |
| Phase | Liquid | Liquid |
| Temp., °F. | 14.0 | 35.1 |
| Pressure, psig | 710.5 | 710.5 |
| Flowrate, lbmol/hr | 212.44 | 3426.74 |
| Component Flow, lbmol/hr | | |
| $CH_4$ | 5.94 | 24.24 |
| $CO_2$ | 39.35 | 276.73 |
| $N_2$ | 0.72 | 2.17 |
| $H_2O$ | 12.63 | 4.82 |
| CO | 1.58 | 4.78 |
| $H_2$ | 1.26 | 4.83 |
| $CH_4O$ | 39.73 | 2944.28 |
| DME | 111.22 | 164.89 |

The light end in the stream of condensate from the condenser is removed by light end distillation column 1, and the crude DME is purified by DME distillation column 1:

| Fuel Grade DME Product and Recycled Crude Methanol | | |
|---|---|---|
| Stream | DME Product | Methanol & Water |
| Phase | Liquid | Liquid |
| Temp., °F. | 96.4 | 264.4 |
| Pressure, psig | 101.3 | 101.3 |
| Flowrate, lbmol/hr | 110.67 | 52.37 |
| Component Flow, lbmol/hr | | |
| $CH_4$ | 0.00 | 0.00 |
| $CO_2$ | 0.01 | 0.00 |
| $N_2$ | 0.00 | 0.00 |
| $H_2O$ | 0.00 | 12.63 |
| CO | 0.00 | 0.00 |
| $H_2$ | 0.00 | 0.00 |
| $CH_4O$ | 0.00 | 39.74 |
| DME | 110.67 | 0.00 |

The methanol & water stream obtained from the bottom of the distillation column is recycled to the DME fluid pluralized bed reactor.

Similarly, the light end in the stream of rich solvent from the methanol absorber is removed by light end distillation column 2, and the crude DME is purified by DME distillation column 2:

| Fuel Grade DME Product and Regenerated Absorption Solvent | | |
|---|---|---|
| Stream | DME Product | Absorption Solvent |
| Phase | Liquid | Liquid |
| Temp., °F. | 96.4 | 260.1 |
| Pressure, psig | 101.3 | 101.3 |
| Flowrate, lbmol/hr | 160.70 | 2953.00 |
| Component Flow, lbmol/hr | | |
| $CH_4$ | 0.00 | 0.00 |
| $CO_2$ | 0.00 | 0.00 |
| $N_2$ | 0.00 | 0.00 |
| $H_2O$ | 0.00 | 4.82 |
| CO | 0.00 | 0.00 |
| $H_2$ | 0.00 | 0.00 |
| $CH_4O$ | 0.00 | 2944.28 |
| DME | 160.70 | 3.90 |

The absorption solvent thus regenerated is recycled to the methanol absorber for reuse. The DME produced (150 tons/day) from these two DME distillation columns has a purity greater than 99.98 mol % which is suitable for fuel grade DME applications.

Figure 3:
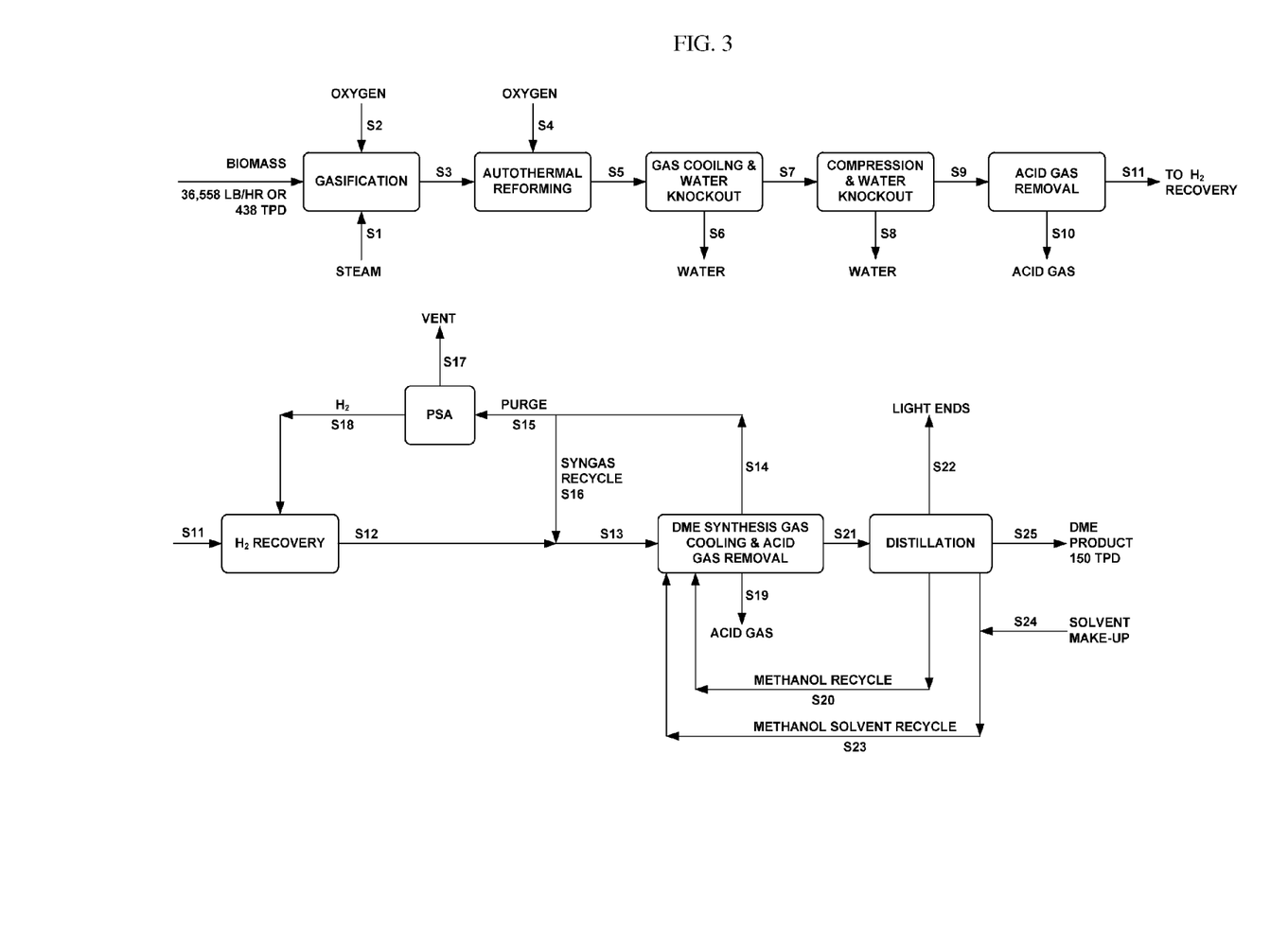
FIG. 3 is a simplified process flow block diagram for the production of 150 tons/day of fuel grade DME from biomass.

A simplified process flow block diagram for the production of 150 tons/day of fuel grade DME from biomass is shown in FIG. 3. This process was simulated using Aspen Plus Version 7.1. The corresponding stream description is shown in Table 1.

Figure 4:
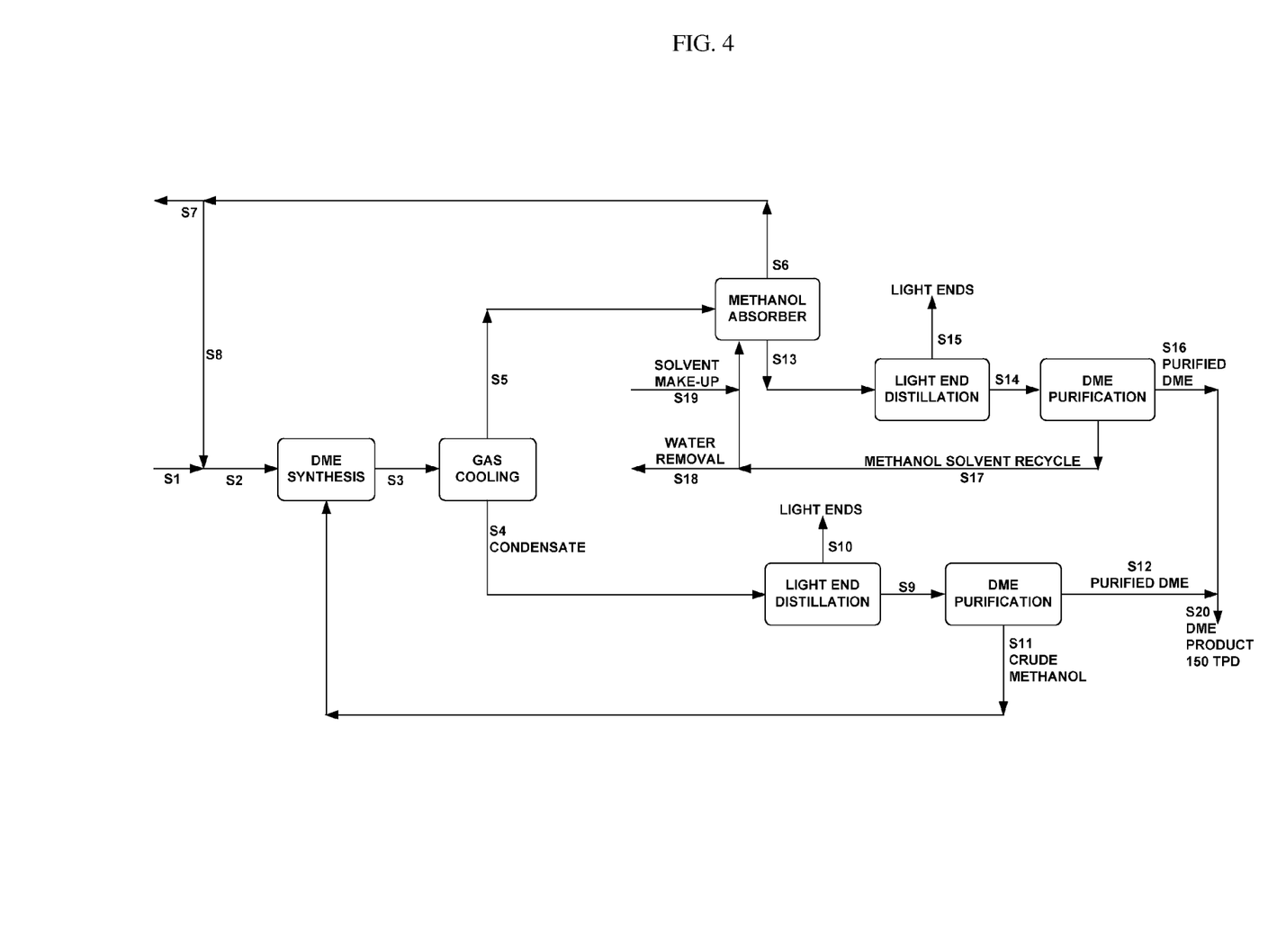
FIG. 4 is a detailed process flow block diagram for the DME synthesis, gas cooling, acid gas removal and DME purification sections.

A detailed process flow block diagram for the DME synthesis, gas cooling, acid gas removal and DME purification sections is shown in FIG. 4 and its corresponding stream description in Table 2.

TABLE 1

| 150 TPD DME PLANT | | | | | | | | |
|---|---|---|---|---|---|---|---|---|
| | Stream No. | | | | | | | |
| | S1 | S2 | S3 | S4 | S5 | S6 | S7 | S8 |
| Phase | V | V | V | V | V | L | V | L |
| Temperature °F. | 800 | 350 | 1750 | 350 | 1557 | 108 | 108 | 108 |
| Pressure, psig | 150 | 150 | 150 | 150 | 144 | 135 | 135 | 284 |
| Flowrate, #mol/hr | 238.5294 | 394.4257 | 2423.1599 | 29.0630 | 2637.6238 | 386.3010 | 2251.3236 | 12.4345 |
| Composition, mol % | | | | | | | | |
| $CH_4$ | 0.0000 | 0.0000 | 6.5902 | 0.0000 | 1.9992 | 0.0000 | 2.3423 | 0.0000 |
| $CO_2$ | 0.0000 | 0.0000 | 16.3313 | 0.0000 | 14.7950 | 0.0000 | 17.3311 | 0.0000 |
| $N_2$ | 0.0000 | 2.0000 | 0.3540 | 2.0000 | 0.3466 | 0.0000 | 0.4060 | 0.0000 |
| $O_2$ | 0.0000 | 98.0000 | 0.0000 | 98.0000 | 0.0000 | 0.0000 | 0.0000 | 0.0000 |
| $H_2O$ | 100.0000 | 0.0000 | 18.4786 | 0.0000 | 15.2890 | 100.0000 | 0.7563 | 100.0000 |
| CO | 0.0000 | 0.0000 | 32.9540 | 0.0000 | 34.5381 | 0.0000 | 40.4644 | 0.0000 |
| $H_2$ | 0.0000 | 0.0000 | 25.2792 | 0.0000 | 33.0191 | 0.0000 | 38.6847 | 0.0000 |
| $H_2S$ | 0.0000 | 0.0000 | 99 PPM | 0.0000 | 91 PPM | 0.0000 | 106 PPM | 0.0000 |
| COS | 0.0000 | 0.0000 | 4 PPM | 0.0000 | 4 PPM | 0.0000 | 5 PPM | 0.0000 |
| $NH_3$ | 0.0000 | 0.0000 | 23 PPM | 0.0000 | 35 PPM | 0.0000 | 41 PPM | 0.0000 |
| $CH_4O$ | 0.0000 | 0.0000 | 0.0000 | 0.0000 | 0.0000 | 0.0000 | 0.0000 | 0.0000 |
| DME | 0.0000 | 0.0000 | 0.0000 | 0.0000 | 0.0000 | 0.0000 | 0.0000 | 0.0000 |
| | Stream No. | | | | | | | |
| | S9 | S10 | S11 | S12 | S13 | S14 | S15 | S16 |
| Phase | V | V | V | V | V | V | V | V |
| Temperature °F. | 108 | 114 | 108 | 100 | 48 | 23 | 23 | 23 |

TABLE 1-continued

150 TPD DME PLANT

|  |  |  |  |  |  |  |  |  |
|---|---|---|---|---|---|---|---|---|
| Pressure, psig | 711 | 0 | 710 | 710 | 710 | 710 | 710 | 710 |
| Flowrate, #mol/hr | 2238.8948 | 487.2304 | 1751.4422 | 1766.3551 | 5302.6448 | 3585.0645 | 48.7748 | 3536.2897 |
| Composition, mol % |  |  |  |  |  |  |  |  |
| $CH_4$ | 2.3553 | 2.6506 | 2.2734 | 2.2543 | 13.9408 | 19.7783 | 19.7783 | 19.7783 |
| $CO_2$ | 17.4271 | 70.3783 | 2.6969 | 2.6741 | 4.8734 | 5.9716 | 5.9716 | 5.9716 |
| $N_2$ | 0.4083 | 0.1511 | 0.4799 | 0.4758 | 7.6955 | 11.3021 | 11.3021 | 11.3021 |
| $O_2$ | 0.0000 | 0.0000 | 0.0000 | 0.0000 | 0.0000 | 0.0000 | 0.0000 | 0.0000 |
| $H_2O$ | 0.2054 | 0.8406 | 197 PPM | 196 PPM | 66 PPM | 1 PPM | 1 PPM | 1 PPM |
| CO | 40.6891 | 16.3485 | 47.4655 | 47.0649 | 30.3942 | 22.0670 | 22.0670 | 22.0670 |
| $H_2$ | 38.8996 | 9.5661 | 47.0646 | 47.5114 | 43.0062 | 40.7562 | 40.7562 | 40.7562 |
| $H_2S$ | 107 PPM | 452 PPM | 0.0000 | 0.0000 | 0.0000 | 0.0000 | 0.0000 | 0.0000 |
| COS | 5 PPM | 22 PPM | 0.0000 | 0.0000 | 0.0000 | 0.0000 | 0.0000 | 0.0000 |
| $NH_3$ | 41 PPM | 173 PPM | 0.0000 | 0.0000 | 0.0000 | 0.0000 | 0.0000 | 0.0000 |
| $CH_4O$ | 0.0000 | 0.0000 | 0.0000 | 0.0000 | 598 PPM | 897 PPM | 897 PPM | 0.0000 |
| DME | 0.0000 | 0.0000 | 0.0000 | 0.0000 | 234 PPM | 351 PPM | 351 PPM | 0.0000 |

| | Stream No. | | | | | | | | |
|---|---|---|---|---|---|---|---|---|---|
| | S17 | S18 | S19 | S20 | S21 | S22 | S23 | S24 | S25 |
| Phase | V | V | V | L | V + L | V | L | L | L |
| Temperature °F. | 23 | 23 | −56 | 100 | 33 | −51 | 260 | 14 | 96 |
| Pressure, psig | 710 | 710 | 101 | 710 | 101 | 101 | 101 | 710 | 101 |
| Flowrate, #mol/hr | 33.8657 | 14.9091 | 313.0383 | 52.7272 | 3639.1756 | 49.3894 | 2953.0180 | 1.9730 | 271.3786 |
| Composition, mol % | | | | | | | | | |
| $CH_4$ | 28.4855 | 0.0000 | 7.7423 | 0.0000 | 0.8293 | 12.0315 | 0.0000 | 0.0000 | 0.0000 |
| $CO_2$ | 8.6005 | 0.0000 | 88.4006 | 0.0000 | 8.6854 | 79.6639 | 0.0000 | 0.0000 | 2 PPM |
| $N_2$ | 16.2778 | 0.0000 | 0.6918 | 0.0000 | 792 PPM | 1.4569 | 0.0000 | 0.0000 | 0.0000 |
| $O_2$ | 0.0000 | 0.0000 | 0.0000 | 0.0000 | 0.0000 | 0.0000 | 0.0000 | 0.0000 | 0.0000 |
| $H_2O$ | 1 PPM | 0.0000 | 0.0000 | 23.9567 | 0.4796 | 0.0000 | 0.1633 | 0.0000 | 12 PPM |
| CO | 31.7818 | 0.0000 | 1.5272 | 0.0000 | 0.1749 | 3.2056 | 0.0000 | 0.0000 | 0.0000 |
| $H_2$ | 14.6747 | 100.0000 | 1.5429 | 0.0000 | 0.1673 | 2.5451 | 0.0000 | 0.0000 | 0.0000 |
| $H_2S$ | 0.0000 | 0.0000 | 0.0000 | 0.0000 | 0.0000 | 0.0000 | 0.0000 | 0.0000 | 0.0000 |
| COS | 0.0000 | 0.0000 | 0.0000 | 0.0000 | 0.0000 | 0.0000 | 0.0000 | 0.0000 | 0.0000 |
| $NH_3$ | 0.0000 | 0.0000 | 0.0000 | 0.0000 | 0.0000 | 0.0000 | 0.0000 | 0.0000 | 0.0000 |
| $CH_4O$ | 0.1292 | 0.0000 | 0.0000 | 75.3623 | 81.9971 | 0.0000 | 99.7043 | 100.0000 | 4 PPM |
| DME | 505 PPM | 0.0000 | 953 PPM | 0.6810 | 7.5873 | 1.0972 | 0.1324 | 0.0000 | 99.9982 |

TABLE 2

150 TPD DME PLANT

| | Stream No. | | | | | | | | | |
|---|---|---|---|---|---|---|---|---|---|---|
| | S1 | S2 | S3 | S4 | S5 | S6 | S7 | S8 | S9 | S10 |
| Phase | V | V | V | L | V | V | V | V | L | V |
| Temperature °F. | 100 | 48 | 500 | 14 | 14 | 23 | 23 | 23 | 116 | −51 |
| Pressure, psig | 710 | 710 | 710 | 710 | 710 | 710 | 710 | 710 | 101 | 101 |
| Flowrate, lbmol/hr | 1766.3551 | 5302.6448 | 4270.1830 | 212.4433 | 4057.6448 | 3585.0645 | 48.7748 | 3536.2897 | 163.0440 | 49.3894 |
| Composition, mol % | | | | | | | | | | |
| $CH_4$ | 2.2554 | 13.9408 | 17.3117 | 2.7974 | 18.0716 | 19.7783 | 19.7783 | 19.7783 | 0.0000 | 12.0315 |
| $CO_2$ | 2.6741 | 4.8734 | 12.4154 | 18.5221 | 12.0957 | 5.9716 | 5.9716 | 5.9716 | 3 PPM | 79.6639 |
| $N_2$ | 0.4758 | 7.6955 | 9.5563 | 0.3387 | 10.0389 | 11.3021 | 11.3021 | 11.3021 | 0.0000 | 1.4569 |
| $H_2O$ | 196 PPM | 66 PPM | 0.3177 | 5.9462 | 230 PPM | 1 PPM | 1 PPM | 1 PPM | 7.7478 | 0.0000 |
| CO | 47.0649 | 30.3942 | 18.6755 | 0.7453 | 19.6142 | 22.0670 | 22.0670 | 22.0670 | 0.0000 | 3.2056 |
| $H_2$ | 47.5114 | 43.0062 | 34.3597 | 0.5917 | 36.1277 | 40.7562 | 40.7562 | 40.7562 | 0.0000 | 2.5451 |
| $CH_4O$ | 0.0000 | 0.0000 | 0.9597 | 18.7045 | 306 PPM | 897 PPM | 897 PPM | 897 PPM | 24.3712 | 0.0000 |
| DME | 0.0000 | 0.0000 | 6.4040 | 52.3540 | 3.9983 | 351 PPM | 351 PPM | 351 PPM | 67.8806 | 1.0972 |

| | Stream No. | | | | | | | | | |
|---|---|---|---|---|---|---|---|---|---|---|
| | S11 | S12 | S13 | S14 | S15 | S16 | S17 | S18 | S19 | S20 |
| Phase | L | L | L | L | V | L | L | L | L | L |
| Temperature °F. | 259 | 96 | 35 | 234 | −56 | 96 | 260 | 260 | 14 | 96 |
| Pressure, psig | 101 | 101 | 710 | 101 | 101 | 101 | 101 | 101 | 710 | 101 |
| Flowrate, lbmol/hr | 52.7272 | 110.6786 | 3426.7323 | 3113.6980 | 313.0383 | 160.7000 | 2953.0180 | 0.9288 | 1.9730 | 271.3786 |

TABLE 2-continued

150 TPD DME PLANT

Composition, mol %

| | | | | | | | | | | |
|---|---|---|---|---|---|---|---|---|---|---|
| $CH_4$ | 0.0000 | 0.0000 | 0.7073 | 0.0000 | 7.7423 | 0.0000 | 0.0000 | 0.0000 | 0.0000 | 0.0000 |
| $CO_2$ | 0.0000 | 5 PPM | 8.0756 | 0.0000 | 88.4006 | 0.0000 | 0.0000 | 0.0000 | 0.0000 | 2 PPM |
| $N_2$ | 0.0000 | 0.0000 | 632 PPM | 0.0000 | 0.6918 | 0.0000 | 0.0000 | 0.0000 | 0.0000 | 0.0000 |
| $H_2O$ | 23.9567 | 29 PPM | 0.1407 | 0.1549 | 0.0000 | 0.0000 | 0.1633 | 100.0000 | 0.0000 | 12 PPM |
| CO | 0.0000 | 0.0000 | 0.1395 | 0.0000 | 1.5272 | 0.0000 | 0.0000 | 0.0000 | 0.0000 | 0.0000 |
| $H_2$ | 0.0000 | 0.0000 | 0.1409 | 0.0000 | 1.5429 | 0.0000 | 0.0000 | 0.0000 | 0.0000 | 0.0000 |
| $CH_4O$ | 75.3623 | 0.0000 | 85.9209 | 94.5590 | 0.0000 | 7 PPM | 99.7043 | 0.0000 | 100.0000 | 4 PPM |
| DME | 0.6810 | 99.9966 | 4.8119 | 5.2861 | 953 PPM | 99.9992 | 0.1324 | 0.0000 | 0.0000 | 99.9982 |

EXAMPLE 2

Same as Example 1 except that the internal heat transmission tube in the fluid pluralized bed reactor is removed. A higher recycle rate (from 3536 μmol/hr to 6363 μmol/hr) in the DME synthesis loop is required to maintain the same effluent temperature of the DME reactor. This higher recycle rate is obtained by injecting more steam to the gasifier (from 239 μmol/hr to 378 μmol/hr). The $H_2/CO$ molar ratio in the feed syngas to the DME reactor also increases from 1.4149 to 2.8088 due to the water gas shift reaction:

Feed Gases to DME Reactor

| Feed Gas to DME Reactor | Example 1 | Example 2 |
|---|---|---|
| Phase | Vapor | Vapor |
| Temp., °F. | 47.5 | 39.5 |
| Pressure, psig | 710.5 | 710.5 |
| Flowrate, lbmol/hr | 5302.72 | 8183.06 |
| $H_2/CO$ Molar Ratio | 1.4149 | 2.8088 |
| Composition, Mol % | | |
| $CH_4$ | 13.94 | 13.46 |
| $CO_2$ | 4.87 | 4.91 |
| $N_2$ | 7.70 | 5.89 |
| $H_2O$ | 0.00 | 0.00 |
| CO | 30.40 | 19.86 |
| $H_2$ | 43.01 | 55.79 |
| $CH_4O$ | 0.06 | 0.07 |
| DME | 0.02 | 0.02 |

The higher recycle rate in the DME synthesis loop also reduces the partial pressure of the DME product in the phase separator, only 0.715 mol % of the DME produced is condensed out in the DME reactor effluent condenser compared to 40.672 mol % in Example 1:

Condensate from the Phase Separator

| Feed Gas to DME Reactor | Example 1 | Example 2 |
|---|---|---|
| Phase | Liquid | Liquid |
| Temp., °F. | 14.0 | 14.0 |
| Pressure, psig | 710.5 | 710.5 |
| Flowrate, lbmol/hr | 212.44 | 79.86 |
| Component Flow, lbmol/hr | | |
| $CH_4$ | 5.94 | 0.07 |
| $CO_2$ | 39.35 | 2.02 |
| $N_2$ | 0.72 | 0.00 |
| $H_2O$ | 12.63 | 37.99 |
| CO | 1.58 | 0.01 |
| $H_2$ | 1.26 | 0.02 |
| $CH_4O$ | 39.74 | 37.78 |
| DME | 111.22 | 1.97 |

Therefore, a higher methanol solvent flowrate is needed in Example 2 for the methanol absorber to absorb the additional DME content in the recycle syngas, 3935 μmol/hr as compared to 2953 μmol/hr in Example 1.

The DME and most of the $CH_4O$ in the condensate from the condenser can be recovered by a distillation column and are recycled back to the DME reactor:

Recovered DME and $CH_4O$ Recycled to DME Reactor

| Phase | Vapor |
|---|---|
| Temp., °F. | 100.0 |
| Pressure, psig | 710.5 |
| Flowrate, lbmol/hr | 38.00 |
| Component Flow, lbmol/hr | |
| $CH_4$ | 0.07 |
| $CO_2$ | 2.02 |
| $N_2$ | 0.00 |
| $H_2O$ | 2.05 |
| CO | 0.01 |
| $H_2$ | 0.02 |
| $CH_4O$ | 31.86 |
| DME | 1.97 |

The light end in the stream of rich solvent from the methanol absorber bottom is separated by a light end distillation column, and the crude DME is purified by the DME distillation column:

Fuel Grade DME Product & Regenerated Absorption Solvent

| Stream | DME Product | Absorption Solvent |
|---|---|---|
| Phase | Liquid | Liquid |
| Temp., °F. | 96.5 | 260.3 |
| Pressure, psig | 101.3 | 101.3 |
| Flowrate, lbmol/hr | 271.40 | 3935.44 |
| Component Flow, lbmol/hr | | |
| $CH_4$ | 0.00 | 0.00 |
| $CO_2$ | 0.01 | 0.00 |
| $N_2$ | 0.00 | 0.00 |
| $H_2O$ | 0.00 | 3.46 |
| CO | 0.00 | 0.00 |
| $H_2$ | 0.00 | 0.00 |
| $CH_4O$ | 0.00 | 3928.38 |
| DME | 271.39 | 3.60 |

In this example, all the DME is produced from a single DME distillation column. The absorption solvent thus regenerated at the column bottom is recycled to the methanol absorber for reuse.

EXAMPLE 3

Same as Example 2 except that the absorption solvent in the methanol absorber is replaced by $CH_3-O(-CH_2-CH_2-O)_5-CH_3$ ($C_{12}H_{26}O_6$). Due to the higher solubility of the syngas in $C_{12}H_{26}O_6$, more biomass, oxygen and steam are required to produce the same amount of DME product:

| Rich Solvent from Methanol/$C_{12}H_{26}O_6$ Absorber | | | |
|---|---|---|---|
| Rich Solvent from Methanol/$C_{12}H_{26}O_6$ Absorber | Example 1 | Example 2 | Example 3 |
| Phase | Liquid | Liquid | Liquid |
| Temp., °F. | 35.1 | 34.3 | 32.0 |
| Pressure, psig | 710.5 | 710.5 | 710.5 |
| Flowrate, lbmol/hr | 3426.74 | 4533.33 | 2358.64 |
| Flowrate, #/hr | 114796 | 151721 | 479062 |
| Wt Ratio, wt % | 23.96 | 31.67 | 100.00 |
| Component Flow, lbmol/hr | | | |
| $CH_4$ | 24.24 | 27.92 | 38.16 |
| $CO_2$ | 276.73 | 283.49 | 280.64 |
| $N_2$ | 2.17 | 1.93 | 5.03 |
| $H_2O$ | 4.82 | 3.46 | 0.71 |
| CO | 4.78 | 3.83 | 17.11 |
| $H_2$ | 4.83 | 9.08 | 42.24 |
| $CH_4O$ | 2944.28 | 3928.38 | 3.17 |
| DME | 164.89 | 275.24 | 271.58 |
| $C_6H_{26}O_6$ | 0.00 | 0.00 | 1700.00 |

| Feedstocks | | | |
|---|---|---|---|
| Feedstocks | Example 1 | Example 2 | Example 3 |
| Biomass (10 wt % moisture), TPD | 438 | 445 | 464 |
| Oxygen (98 mol % pure), TPD | 162 | 164 | 170 |
| Steam, TPD | 52 | 82 | 100 |

The absorption solvent $C_{12}H_{26}O_6$ also has much higher molecular weight and boiling point than $CH_4O$ which means higher energy is required to heat, to cool and to pump the absorption solvent $C_{12}H_{26}O_6$:

| Pure Absorption Solvent Physical Properties | | | | |
|---|---|---|---|---|
| Absorption Solvent | MW | TF, °F. | TB, °F. | ΔHv, Btu/#mol |
| $CH_4O$ | 32.04 | −143.82 | 148.46 | 15108 |
| $C_{12}H_{26}O_6$ | 266.33 | 11.21 | 647.51 | 29585 |

| Energy Requirement | | | |
|---|---|---|---|
| Energy Requirement | Example 1 | Example 2 | Example 3 |
| Reboiler Heat Duty, Btu/hr | 31.88 × 10⁶ | 48.72 × 10⁶ | 230.07 × 10⁶ |
| To Pump from 101 psig to 710 psig, hp | 157.16 | 209.57 | 855.86 |
| To Cool from Reboiler Temp. to 14° F., Btu/hr | 20.79 × 10⁶ | 27.74 × 10⁶ | 212.60 × 10⁶ |

EXAMPLE 4

Same as Example 2 except that 18.75 mol % of the cooled syngas from the autothermal reformer is passed through a water gas shift (WGS) reactor. The effluent from the WGS reactor is then combined with the remaining 81.25 mol % of the syngas in order to have a similar compressed syngas composition as in Example 2:

| Compressed Syngas Composition | | |
|---|---|---|
| Compressed Syngas Composition | Example 2 | Example 4 |
| Phase | Vapor | Vapor |
| Temp., °F. | 108.0 | 108.0 |
| Pressure, psig | 710.5 | 710.5 |
| Component Flow, lbmol/hr | | |
| $CH_4$ | 56.26 | 52.76 |
| $CO_2$ | 445.19 | 444.35 |
| $N_2$ | 9.23 | 9.24 |
| $H_2O$ | 4.79 | 4.78 |
| CO | 873.48 | 871.69 |
| $H_2$ | 930.05 | 930.94 |

Meanwhile the steam feed to the gasifier is greatly reduced:

| Steam Feed to Gasifier | | |
|---|---|---|
| Feedstocks | Example 2 | Example 4 |
| Steam, TPD | 82 | 46 |

EXAMPLE 5

Same as Example 1 except that the PSA unit for the $H_2$ recovery from the DME synthesis loop purge gas is eliminated and the whole purge gas stream is recycled to the autothermal reformer. The methane content in the purge gas is reformed to produce more $H_2$ and CO in the autothermal reformer, and less biomass, oxygen and steam are required to produce the same amount of DME product.

| Feedstocks | | |
|---|---|---|
| Feedstocks | Example 1 | Example 5 |
| Biomass (10 wt % moisture), TPD | 438 | 429 |
| Oxygen (98 mol % pure), TPD | 162 | 161 |
| Steam, TPD | 52 | 50 |

The $H_2$/CO molar ratio in the feed syngas to the DME reactor also reduces from 1.4149 to 1.0392 due to the elimination of the PSA unit for the $H_2$ recovery from the purge gas. Meanwhile the $N_2$ concentration increases from 7.70 to 19.12 mol %.

| Feed Gases to DME Reactor | | |
|---|---|---|
| Feed Gas to DME Reactor | Example 1 | Example 5 |
| Phase | Vapor | Vapor |
| Temp., °F. | 47.5 | 46.6 |
| Pressure, psig | 710.5 | 710.5 |
| Flowrate, lbmol/hr | 5302.72 | 5308.02 |
| $H_2$/CO Molar Ratio | 1.4149 | 1.0392 |
| Composition, Mol % | | |
| $CH_4$ | 13.94 | 14.00 |
| $CO_2$ | 4.87 | 4.95 |
| $N_2$ | 7.70 | 19.12 |
| $H_2O$ | 0.00 | 0.00 |
| CO | 30.40 | 30.33 |

-continued

Feed Gases to DME Reactor

| Feed Gas to DME Reactor | Example 1 | Example 5 |
|---|---|---|
| $H_2$ | 43.01 | 31.52 |
| $CH_4O$ | 0.06 | 0.06 |
| DME | 0.02 | 0.02 |

EXAMPLE 6

Same as Example 1 except that the pressure of the two light end columns is changed to 224.6 psig, 347.9 psig and 463.9 psig in order to increase the condenser temperature. The pressures and the resulting molar reflux ratios, temperatures and heat duties of the condensers and reboilers for these two light end columns are shown below:

LIGHT END DISTILLATION COLUMN #1

| | | Condenser | | Reboiler | |
|---|---|---|---|---|---|
| Pressure, Bar (psig) | Molar Reflux Ratio | Temperature, °F. | Heat Duty, $10^6$ Btu/hr | Temperature, °F. | Heat Duty, $10^6$ Btu/hr |
| 8.0 (101.3) | 1.0 | −50.92 | −0.38 | 116.14 | 0.99 |
| 16.5 (224.6) | 2.0 | −18.15 | −0.65 | 175.05 | 1.55 |
| 25.0 (347.9) | 3.0 | −0.66 | −1.08 | 214.27 | 1.57 |
| 33.0 (463.9) | 4.0 | 18.13 | −1.05 | 243.40 | 2.30 |

LIGHT END DISTILLATION COLUMN #2

| | | Condenser | | Reboiler | |
|---|---|---|---|---|---|
| Pressure, Bar (psig) | Molar Reflux Ratio | Temperature, °F. | Heat Duty, $10^6$ Btu/hr | Temperature, °F. | Heat Duty, $10^6$ Btu/hr |
| 8.0 (101.3) | 1.0 | −55.54 | −2.05 | 233.77 | 20.32 |
| 16.5 (224.6) | 2.0 | −20.46 | −3.65 | 293.31 | 28.04 |
| 25.0 (347.9) | 2.5 | 1.58 | −4.11 | 330.61 | 31.06 |
| 33.0 (463.9) | 3.0 | 19.01 | −4.43 | 357.64 | 36.31 |

EXAMPLE 7

Same as Example 5 except that the Australian brown coal (sometimes the brown coal is called lignite) is used to replace the biomass feed. Brown coal is a relatively soft material that has a heating value only about one-quarter of that of black coal. The typical composition of an Australian brown coal is shown below:

Brown Coal Proximate Analyses

| Comp. | Wt % |
|---|---|
| Moisture | 0.00 |
| Fixed Carbon | 25.87 |
| Volatiles | 70.13 |
| Ash | 4.00 |
| Total | 100.00 |

Brown Coal Ultimate Analyses

| Comp. | Wt % |
|---|---|
| Carbon | 66.0 |
| Hydrogen | 4.5 |
| Nitrogen | 0.5 |
| Sulfur | 1.0 |
| Oxygen | 24.0 |
| Ash | 4.0 |
| Total | 100.0 |

Due to the higher carbon and lower oxygen contents in the brown coal ultimate analyses, less brown coal and more steam are required to produce the same amount of DME product:

Feedstocks

| Feedstocks | Example 5 | Example 7 |
|---|---|---|
| Dry Solid Feed, TPD | 386 | 267 |
| Oxygen (98 mol % pure), TPD | 161 | 136 |
| Steam, TPD | 50 | 167 |

EXAMPLE 8

Same as Example 5 except that the natural gas with the following typical composition is used to replace the biomass feed. Since natural gas is rich in hydrogen, the syngas thus produced has a hydrogen to carbon monoxide molar ratio of 3 to 4. In order to have a molar ratio of about 1, a lot of carbon dioxide is needed to shift the following reaction to the left:

$$CO+H_2O \Leftrightarrow CO_2+H_2$$

Typical Natural Gas Composition

| Component | Mole % |
|---|---|
| Methane | 95.2 |
| Ethane | 2.5 |
| Nitrogen | 1.3 |
| Carbon Dioxide | 0.7 |
| Propane Plus | 0.3 |
| Total | 100.0 |
| Specific Gravity | 0.58 |
| Gross Heating Value | 37.8 MJ/m³ (dry) |

Due to the higher heating value of natural gas (23276 Btu/lb) as compared to brown coal (11130 Btu/lb) or biomass (8225 Btu/lb), much less of natural gas is required to produce the same amount of DME product.

Feedstocks

| Feedstocks | Example 5 | Example 7 | Example 8 |
|---|---|---|---|
| Fuel, TPD | 386 | 267 | 133 |
| Oxygen (98 mol % pure), TPD | 161 | 136 | 179 |
| Steam, TPD | 50 | 167 | — |
| Carbon Dioxide, TPD | — | — | 272 |

EXAMPLE 9

Same as Example 8 except that the high carbon dioxide content streams of the acid gas removal unit off gas and the light end distillation column overhead are used to replace the pure carbon dioxide feed. Meanwhile additional hydrogen and carbon monoxide in these two streams are also recovered, thus less natural gas feed is required. In addition, much less carbon dioxide (the greenhouse gas) is rejected to the environment.

Feedstocks & Carbon Dioxide Released to the Environment

| Feedstocks | Example 5 | Example 7 | Example 8 | Example 9 |
|---|---|---|---|---|
| Fuel, TPD | 386 | 267 | 133 | 126 |
| Oxygen (98 mol % pure), TPD | 161 | 136 | 179 | 171 |
| Steam, TPD | 50 | 167 | — | — |
| Carbon Dioxide, TPD | — | — | 272 | 276 |
| Addition Hydrogen & Carbon Monoxide Recovered, TPD | — | — | — | 23 |
| Carbon Dioxide (Greenhouse Gas) Released to the Environment for the Production of DME, TPD | 413 | 361 | 339 | 51 |
| Net Carbon Dioxide Released to the Environment after Combustion of DME, TPD | 0 | 648 | 626 | 338 |

Thus using the recycle of the carbon dioxide rich streams to replace pure carbon dioxide feed stream in the production of DME from natural gas releases the minimum amount of greenhouse gas to the environment. It should be noted that the combustion of DME also releases carbon dioxide (287 TPD). However, the amount of carbon dioxide released during the production and the combustion of DME is balanced exactly the amount of carbon dioxide consumed during the lifecycle of the biomass used to produce DME. Therefore, use of DME made from biomass as an energy source causes no net increase in the carbon dioxide levels of the atmosphere.

EXAMPLE 10

Same as Example 1 except that the two DME distillation columns are replaced by a single light and DME distillation column. The regenerated solvents in both cases are first cooled by the two cold streams fed to the light end columns before the final cooling to the absorber inlet temperature. Since the regenerated solvent in Example 10 contains about 1.25 wt % of DME and gives a higher partial pressure of DME in the treated recycle gas, thus a lower temperature such as −20° F. is required for the absorber inlet temperature.

Energy Requirement

| Heat Duties | Example 1 | Example 10 |
|---|---|---|
| Regenerated Solvent Flowrate, lbmol/hr | 2988 | 1715 |
| Absorber Inlet Temp., ° F. | 14 | −20 |
| Total Condenser Heat Duties, $10^6$ Btu/hr | −23.24 | −8.97 |
| Total Reboiler Heat Duties, $10^6$ Btu/hr | 31.40 | 13.32 |
| Cool Reactor Effluent from 100° F. to Absorber Inlet Temperature, $10^6$ Btu/hr | −4.83 | −7.27 |
| Cool Regenerated Solvent from the Light End Heat Exchanger Outlet Temperature to the Absorber Inlet Temperature, $10^6$ Btu/hr | −8.39 | −2.46 |

As can be seen above, there are clear advantages to use the methanol/DME mixture which contains about 1.25 wt % of DME instead of pure methanol as the scrubbing solvent in terms of saving both refrigerating and heating energy.

What is claimed is:

1. A process for making DME product in a fluid pluralized bed reactor, comprising: flowing a syngas containing hydrogen and carbon monoxide through a fluid pluralized bed reactor at a superficial gas velocity ranges from 0.1 msec to 2.0 msec; contacting the syngas with a bifunctional catalyst in a dense phase fluid pluralized bed reactor having a catalyst bed height to diameter ratio of not greater than 10:1 so as to form DME product; and separating the catalyst from the product gas in the disengaging zone via one or more cyclones equipped with diplegs.

2. The process of claim 1, wherein about 75% of the hydrogen content in the purge stream from the DME synthesis loop is recovered via a PSA unit, which is then combined with the fresh make-up syngas.

3. The process of claim 1, wherein the vent from the PSA unit may be fed to the autothermal reformer, thus the methane content in the vent stream is reformed to produce additional hydrogen and carbon monoxide, and the hydrogen and carbon monoxide in the vent stream are conserved.

4. The process of claim 1, wherein the PSA unit for the hydrogen recovery from the DME synthesis loop purge gas is eliminated and the whole purge gas stream is recycled to the autothermal reformer to reform the methane content and conserve the hydrogen and carbon monoxide content in the purge gas stream.

5. The process of claim 1, wherein the feed gases are entering the reactor at several different sections and the flowrates of the different incoming feed gas streams are independently controlled to generate axial isothermality of the reactor.

6. The process of claim 1, wherein the make-up syngas stream flowing into the reactor enters at ambient temperature, 37.8° C., while the recycle syngas enters at DME synthesis loop absorber outlet temperatures ranging from −21° C. to −5° C.

7. The process of claim 1, wherein the positions of the distributors in the fluid pluralized bed reactor are optimally approaching a logarithmic distribution.

8. The process of claim 1, wherein the feed gases flowing through the fluid pluralized bed reactor further contains about 2 mol % to 5 mol % of carbon dioxide to maintain the high activity of the catalyst.

9. The process of claim 1, wherein the bifunctional catalyst has a particle size ranging from 20 to 300 μm.

10. The process of claim 1, wherein the fluid pluralized bed reactor temperature is controlled either with or without the internal heat transmission tube in the reactor.

11. The process of claim 1, wherein the catalyst in the dense phase is maintained at a solid volume fraction ranging from 0.4 to 0.5 and in the lean phase, the catalyst is maintained at a solid volume fraction ranging from 0.2 to 0.25.

12. The process of claim 1, wherein the catalyst that is separated via the cyclones is returned to the dense phase fluid pluralized bed through the diplegs for reuse.

13. The process of claim 1, wherein the fluid pluralized bed reactor is maintained at a temperature ranging from 150° C. to 350° C.

14. The process of claim 1, wherein the fluid pluralized bed reactor is maintained at a pressure ranging from 3 MPa to 8 MPa.

15. The process of claim 1, wherein a water gas shift reactor is added after the autothermal reformer to shift part of the syngas produced in order to reduce the flowrate of steam fed to the gasifier and keep the same hydrogen to carbon monoxide molar ratio.

* * * * *